United States Patent
Locke et al.

(10) Patent No.: US 9,327,063 B2
(45) Date of Patent: May 3, 2016

(54) REDUCED-PRESSURE CANISTERS HAVING HYDROPHOBIC PORES

(75) Inventors: Christopher Brian Locke, Bournemouth (GB); Timothy Mark Robinson, Basingstoke (GB); Richard Daniel John Coulthard, Dorset (GB); Jonathan Paul Jaeb, Boerne, TX (US)

(73) Assignee: KCI Licensing, Inc., San Antonio, TX (US)

( * ) Notice: Subject to any disclaimer, the term of this patent is extended or adjusted under 35 U.S.C. 154(b) by 281 days.

(21) Appl. No.: 13/571,838

(22) Filed: Aug. 10, 2012

(65) Prior Publication Data

US 2013/0066301 A1 Mar. 14, 2013

Related U.S. Application Data

(60) Provisional application No. 61/534,232, filed on Sep. 13, 2011.

(51) Int. Cl.
*A61M 27/00* (2006.01)
*B23P 19/04* (2006.01)
*A61M 1/00* (2006.01)

(52) U.S. Cl.
CPC ........... *A61M 1/0001* (2013.01); *A61M 1/0049* (2013.01); *A61M 1/0052* (2014.02); *A61M 1/0096* (2014.02); *A61M 1/0088* (2013.01); *A61M 2205/7536* (2013.01); *A61M 2205/7563* (2013.01); *A61M 2207/00* (2013.01); *Y10T 29/49888* (2015.01)

(58) Field of Classification Search
USPC ........................................................ 604/543
See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flowe, Jr. |
| 3,568,675 A | 3/1971 | Harvey |
| 3,648,692 A | 3/1972 | Wheeler |

(Continued)

FOREIGN PATENT DOCUMENTS

| AU | 550575 A1 | 8/1982 |
| AU | 745271 | 4/1999 |

(Continued)

OTHER PUBLICATIONS

International Search Report and Written Opinion for corresponding PCT/US2012/050369, mailed Nov. 27, 2012.

(Continued)

*Primary Examiner* — Tatyana Zalukaeva
*Assistant Examiner* — Guy K Townsend

(57) ABSTRACT

A reduced-pressure canister includes a canister body having a fluid reservoir, an inlet for receiving fluids from a patient, and an integral hydrophobic filter formed within a side or top portion of the canister body. The integral hydrophobic filter has a plurality of pores in the canister body that are covered by a hydrophobic coating. Other canisters, methods, and systems are also presented.

19 Claims, 8 Drawing Sheets

(56) References Cited

U.S. PATENT DOCUMENTS

| | | |
|---|---|---|
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,930,997 A * | 6/1990 | Bennett ............... A61M 1/0019 417/410.1 |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,086,764 A * | 2/1992 | Gilman ............... A61F 13/0203 128/888 |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,466,229 A * | 11/1995 | Elson ............... A61M 1/0023 604/257 |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,142,982 A * | 11/2000 | Hunt ............... A61M 1/0023 604/313 |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,648,862 B2 * | 11/2003 | Watson ............... A61M 1/0001 604/319 |
| 6,814,079 B2 | 11/2004 | Heaton et al. |
| 7,063,688 B2 * | 6/2006 | Say ............... A61M 1/0023 604/118 |
| 7,160,273 B2 * | 1/2007 | Greter ............... A61M 1/0001 604/317 |
| 7,316,672 B1 * | 1/2008 | Hunt ............... A61M 1/0023 604/313 |
| 7,503,910 B2 * | 3/2009 | Adahan ............... A61M 1/0066 604/313 |
| 7,611,500 B1 * | 11/2009 | Lina ............... A61M 1/0096 604/304 |
| 7,619,130 B2 * | 11/2009 | Nielsen ............... A61F 13/02 602/41 |
| 7,670,323 B2 * | 3/2010 | Hunt ............... A61M 1/0023 600/131 |
| 7,722,582 B2 * | 5/2010 | Lina ............... A61F 13/0203 602/46 |
| 7,722,584 B2 * | 5/2010 | Tanaka ............... A61F 5/451 604/317 |
| 7,758,554 B2 * | 7/2010 | Lina ............... A61F 13/0203 602/41 |
| 7,857,806 B2 * | 12/2010 | Karpowicz ........... A61M 1/0031 601/6 |
| RE42,834 E * | 10/2011 | Watson ............... A61M 1/0001 604/319 |
| 8,105,295 B2 * | 1/2012 | Blott ............... A61M 1/0088 604/304 |
| 8,235,972 B2 * | 8/2012 | Adahan ............... A61M 1/0066 604/305 |
| 8,240,470 B2 * | 8/2012 | Pidgeon ............... A45C 11/00 206/438 |
| 8,317,774 B2 * | 11/2012 | Adahan ............... A61M 1/0088 604/313 |
| 8,348,910 B2 * | 1/2013 | Blott ............... A61M 1/0058 604/119 |
| 8,622,981 B2 * | 1/2014 | Hartwell ............. A61M 1/0001 128/912 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0153860 A1 * | 8/2003 | Nielsen ............... A61F 13/02 602/43 |
| 2004/0102743 A1 * | 5/2004 | Walker ............... A61L 2/0088 604/319 |
| 2007/0167927 A1 * | 7/2007 | Hunt ............... A61M 1/0023 604/313 |
| 2007/0179460 A1 * | 8/2007 | Adahan ............... A61M 1/0066 604/319 |
| 2007/0202342 A1 * | 8/2007 | Whiteford ............. A01N 43/90 428/425.5 |
| 2007/0272606 A1 * | 11/2007 | Freese ............... B01D 39/1692 210/500.25 |
| 2008/0020127 A1 * | 1/2008 | Whiteford ............. A01N 43/90 427/2.1 |
| 2008/0082061 A1 * | 4/2008 | Zhou ............... A61M 27/00 604/319 |

(56) References Cited

U.S. PATENT DOCUMENTS

| | | | |
|---|---|---|---|
| 2008/0110822 A1* | 5/2008 | Chung | B01D 39/086 210/505 |
| 2008/0281283 A1* | 11/2008 | Walker | A61L 2/0088 604/320 |
| 2009/0198201 A1* | 8/2009 | Adahan | A61M 1/0066 604/319 |
| 2009/0221990 A1 | 9/2009 | Jaeb et al. | |
| 2009/0254054 A1* | 10/2009 | Blott | A61M 1/0001 604/290 |
| 2010/0016767 A1* | 1/2010 | Jones | A61M 1/0031 601/10 |
| 2010/0063483 A1* | 3/2010 | Adahan | A61M 1/0088 604/543 |
| 2010/0305523 A1 | 12/2010 | Vess | |
| 2011/0008179 A1* | 1/2011 | Turner | A61M 1/0031 417/53 |
| 2011/0152799 A1 | 6/2011 | Kevin et al. | |
| 2011/0238004 A1* | 9/2011 | Chewins | A61L 2/0088 604/24 |
| 2011/0313373 A1* | 12/2011 | Riesinger | A61F 13/00068 604/319 |
| 2013/0066301 A1* | 3/2013 | Locke | A61M 1/0001 604/543 |

FOREIGN PATENT DOCUMENTS

| | | | |
|---|---|---|---|
| AU | 455496 | 2/2002 | |
| CA | 2005436 | 6/1990 | |
| DE | 26 40 413 A1 | 3/1978 | |
| DE | 43 06 478 A1 | 9/1994 | |
| DE | 295 04 378 U1 | 10/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 B1 | 8/2004 | |
| GB | 692578 | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 333 965 A | 8/1999 | |
| GB | 2 329 127 B | 8/2000 | |
| JP | 4129536 | 4/1992 | |
| SG | 71559 | 4/2002 | |
| WO | 80/02182 | 10/1980 | |
| WO | 87/04626 | 8/1987 | |
| WO | 90/10424 | 9/1990 | |
| WO | 93/09727 | 5/1993 | |
| WO | 94/20041 | 9/1994 | |
| WO | 96/05873 | 2/1996 | |
| WO | 97/18007 | 5/1997 | |
| WO | 99/13793 | 3/1999 | |
| WO | WO 2009004288 A2 * | 1/2009 | A61M 1/00 |

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ð ukié, Ž. Maksimović, Ð . Radak, and P. Peŝka, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

(56) References Cited

OTHER PUBLICATIONS

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, The Use of Hypermia in the Postoperative Treatment of Lesions of the Extremities and Thorax, Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

* cited by examiner

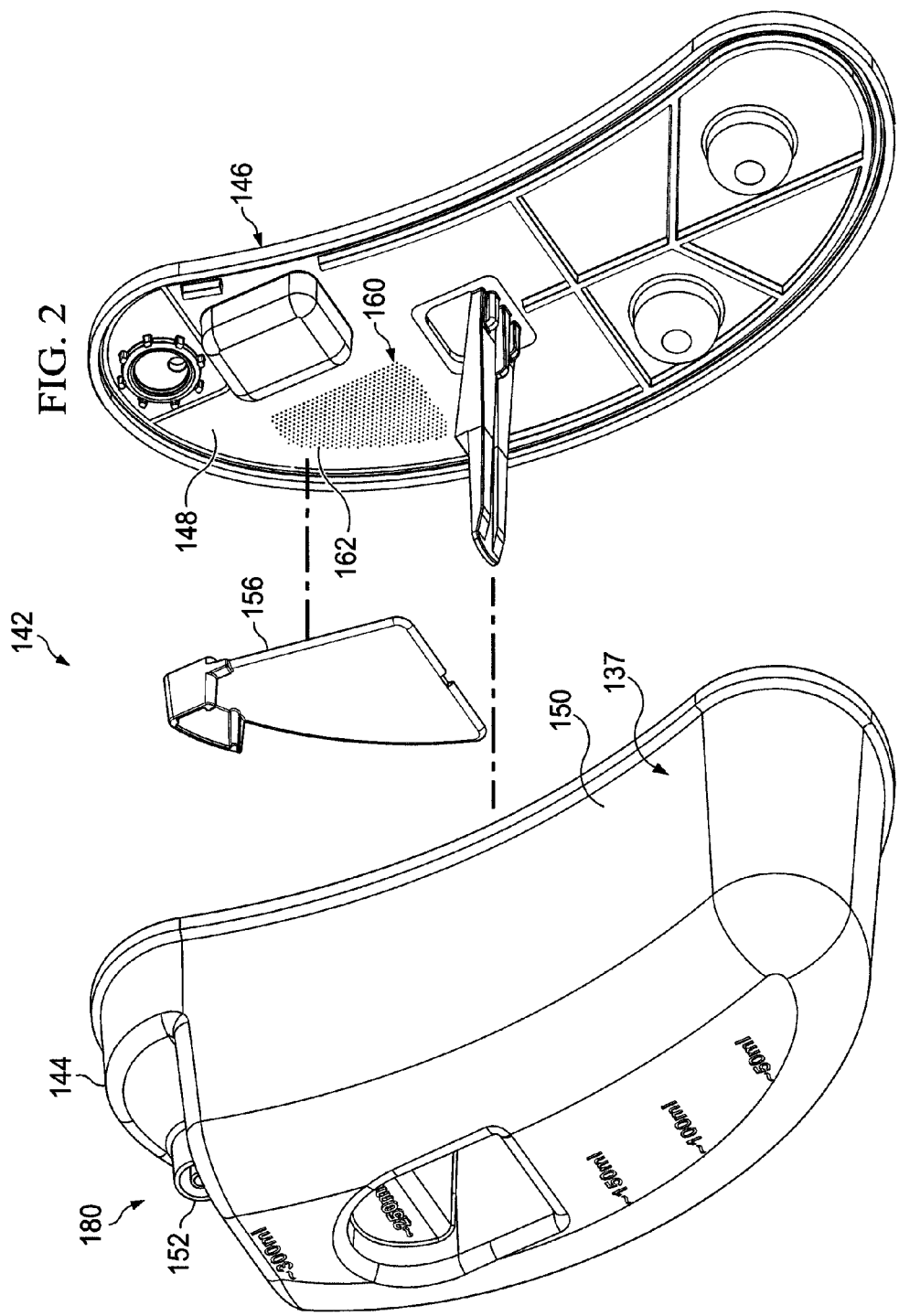

REDUCED-PRESSURE CANISTERS HAVING HYDROPHOBIC PORES

RELATED APPLICATIONS

The present invention claims the benefit, under 35 USC §119(e), of the filing of U.S. Provisional Patent Application Ser. No. 61/534,232, entitled "Reduced-Pressure Canisters Having Hydrophobic Pores," filed Sep. 13, 2011, by Locke et al., which is incorporated herein by reference for all purposes.

FIELD

The present disclosure relates generally to medical treatment systems and, more particularly, but not by way of limitation, to reduced-pressure canisters having hydrophobic pores.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced-pressure therapy," or "vacuum therapy") provides a number of benefits, which may include faster healing and increased formulation of granulation tissue. Typically, reduced pressure is applied to tissue through a porous pad or other manifold device. The porous pad contains cells or pores or pathways that are capable of distributing reduced pressure to the tissue and channeling fluids that are drawn from the tissue. Reduced pressure may also be used for draining fluids or other applications. The fluids removed are typically delivered to a canister.

SUMMARY

According to an illustrative embodiment, a reduced-pressure treatment system includes a reduced-pressure canister. The reduced-pressure canister includes a canister body that forms a fluid reservoir and an inlet for receiving fluids from a patient. The reduced-pressure canister also includes a vent portion that has a plurality of pores and a hydrophobic coating over the plurality of pores. A reduced-pressure source is fluidly coupled to the reduced-pressure canister. The reduced-pressure treatment system also includes a reduced-pressure delivery conduit fluidly coupled to the inlet for delivering fluids from the patient to the reduced-pressure canister.

According to an illustrative embodiment, a method of manufacturing a reduced-pressure canister includes the steps of forming a canister body with a fluid reservoir and an inlet for receiving fluids from a patient. The method also includes forming a vent portion in the canister body. The step of forming the vent portion includes forming a plurality of pores in a boundary area of the canister body and applying a hydrophobic coating over the plurality of pores.

According to an illustrative embodiment, a reduced-pressure canister includes a canister body having a fluid reservoir. The reduced-pressure canister has an inlet for receiving fluids from a patient and an integral hydrophobic filter formed within a side or top portion of the canister body. The integral hydrophobic filter includes a plurality of pores and a hydrophobic coating applied to the plurality of pores.

According to an illustrative embodiment, a method of forming a hydrophobic vent on a reduced-pressure canister includes the steps of forming a plurality of apertures on a canister body and applying a hydrophobic coating to the plurality of apertures. In this illustrative embodiment, the step of applying a hydrophobic coating includes applying a fluorocarbon coating in a plasma treatment process.

Other features and advantages of the illustrative embodiments will become apparent with reference to the drawings and detailed description that follow.

BRIEF DESCRIPTION OF THE DRAWINGS

FIG. 2 is a schematic, exploded, perspective view of the reduced-pressure canister of FIG. 1;

DETAILED DESCRIPTION OF ILLUSTRATIVE EMBODIMENTS

The following detailed description of the illustrative, non-limiting embodiments, makes reference to the accompanying drawings that form a part hereof. These embodiments are described in sufficient detail to enable those skilled in the art to practice the invention, and other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
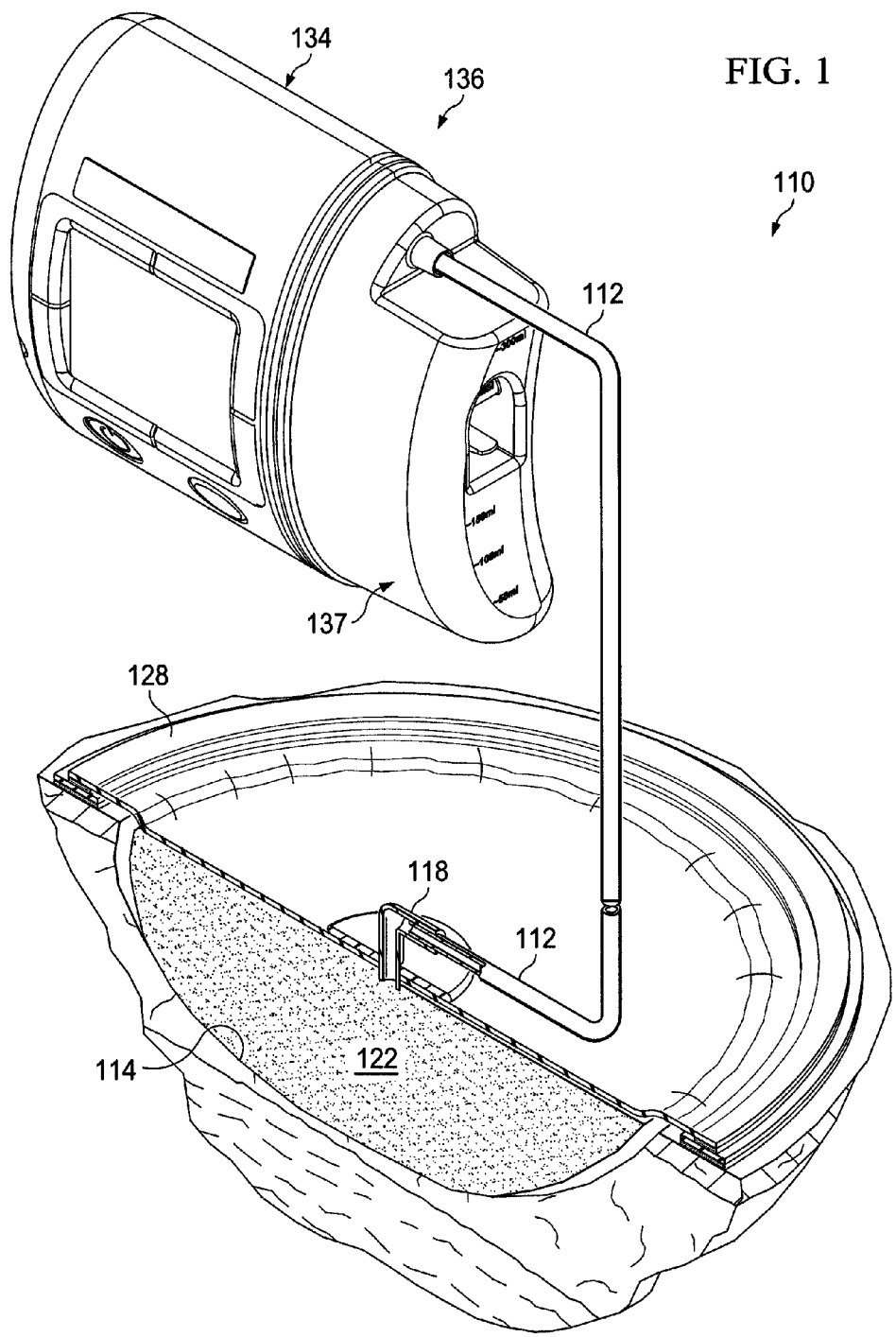
FIG. 1 is a schematic, perspective view, with a portion shown in cross section, of a reduced-pressure treatment system having a reduced-pressure canister according to an illustrative embodiment.

Referring now to the drawings and initially and primarily to FIG. 1, an illustrative embodiment of a reduced-pressure treatment system 110 is presented that includes a reduced-pressure delivery conduit 112 in fluid communication with a tissue site 114 of a patient. The tissue site may be a wound or defect located on or within any tissue, including but not limited to, bone tissue, adipose tissue, muscle tissue, neural tissue, dermal tissue, vascular tissue, connective tissue, cartilage, tendons, or ligaments. The tissue site may also be an area of any tissue, including wounded or defective as well as areas in which it is desired to add or promote the growth of additional tissue. For example, the reduced-pressure treatment system 110 may be used in certain tissue areas to grow additional tissue that may be harvested and transplanted to another tissue location.

The reduced-pressure delivery conduit 112 may fluidly communicate with the tissue site 114 through a tubing adapter 118 and a distribution manifold 122. The distribution manifold 122 may be any material, either bioabsorbable or non-bioabsorbable, if the material is capable of manifolding a reduced pressure to the tissue site 114. In one embodiment, the distribution manifold 122 may be an open-cell, reticulated polyurethane foam. A drape 128 may be placed over the distribution manifold 122 and sealed around a perimeter of the tissue site 114 to maintain reduced pressure at the tissue site 114.

A coupling provides fluid communication between the reduced-pressure delivery conduit 112 and a reduced-pressure source 134. In one implementation, the reduced-pressure source 134 may be a reduced pressure or vacuum pump driven by a motor. In another embodiment, the reduced-pressure source may be a manually-actuated pump such as a compressible bellows pump. In still another embodiment, the reduced-pressure source 134 may be a wall suction port such as are available in hospitals and other medical facilities.

The reduced-pressure source 134 may be housed within a reduced-pressure treatment unit 136, which may also contain sensors, processing units, alarm indicators, memory, databases, software, display units, and user interfaces that further facilitate the application of reduced pressure treatment to the tissue site 114. In one example, a sensor (not shown) may be disposed at or near the reduced-pressure source 134 to determine a source pressure generated by the reduced-pressure source 134. The sensor may communicate with a processing unit that monitors and controls the reduced pressure delivered by the reduced-pressure source 134. Delivery of reduced pressure to the tissue site encourages new tissue growth by maintaining drainage of exudate from the tissue site, increasing blood flow to tissues surrounding the tissue site, and by compressing the distribution manifold into the tissue site, thereby creating microstrain at the tissue site which stimulates new tissue growth.

Figure 3A:
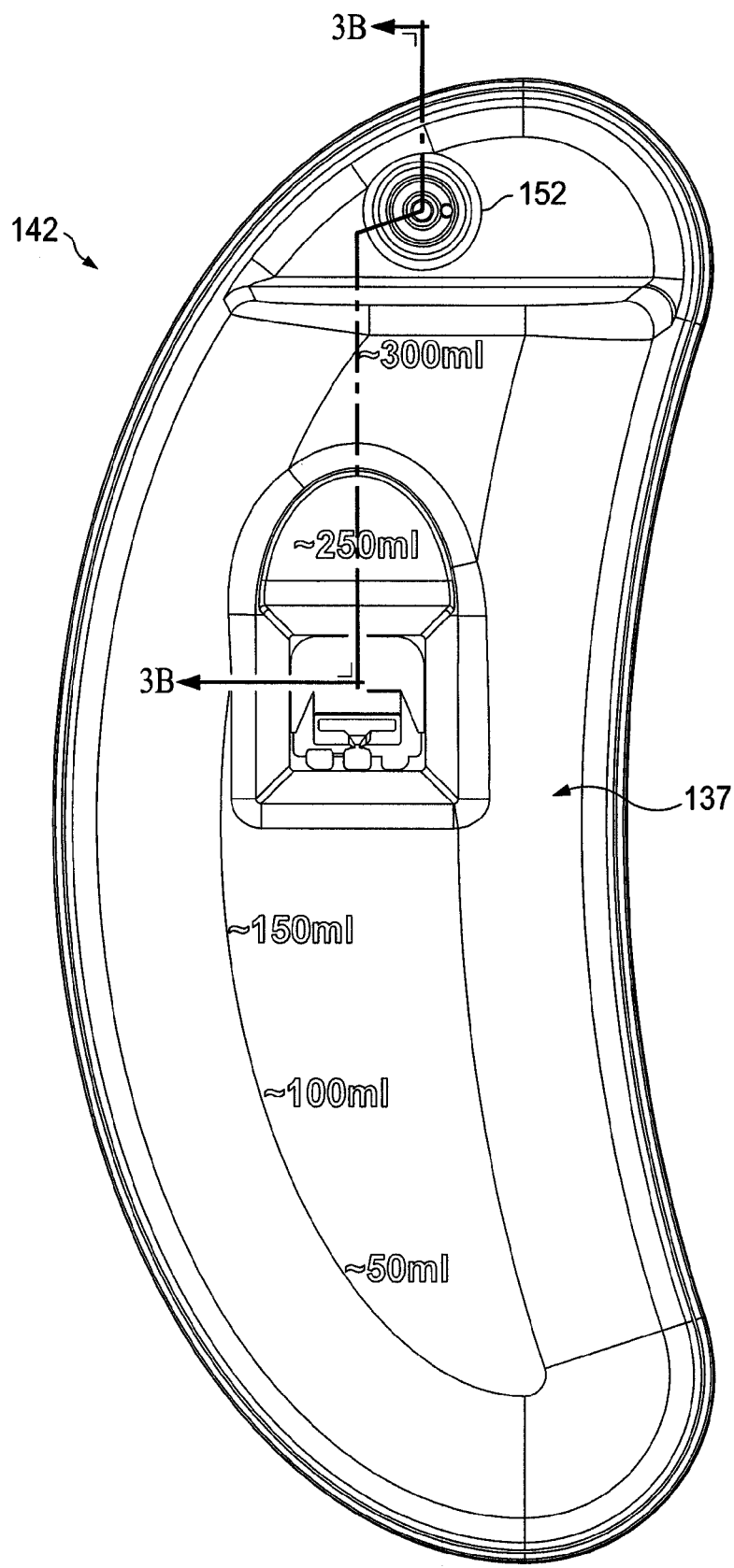
FIG. 3A is a schematic, side perspective view of the reduced-pressure canister of FIGS. 1-2.
Figure 3B:
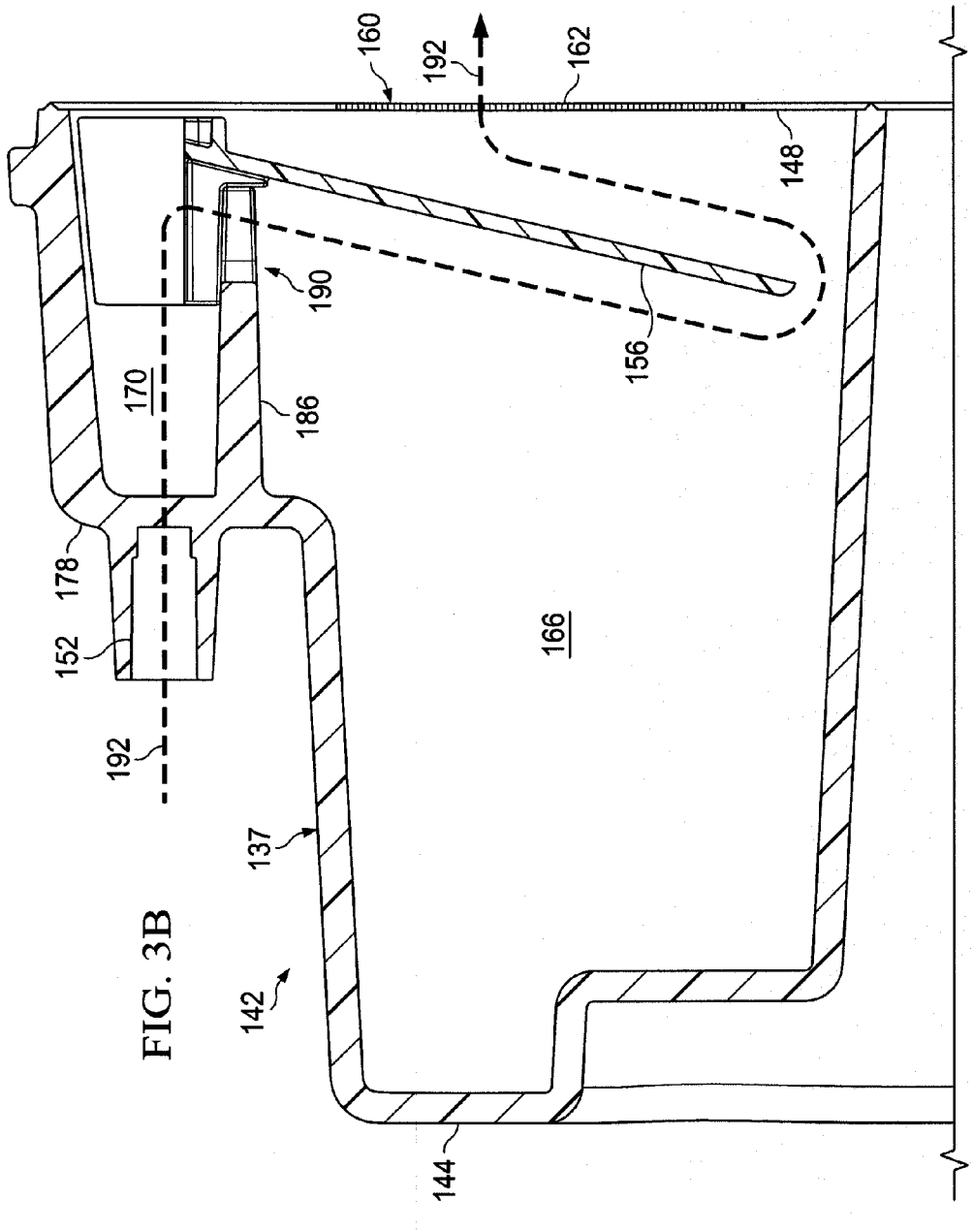
FIG. 3B is a schematic, side view of a portion of the of the reduced-pressure canister of FIG. 1-3A in cross section taken along line 3B-3B of FIG. 3A.

Referring still to FIG. 1, but also to FIGS. 2-3B, a canister 137 having a canister body 142 is fluidly coupled between the reduced-pressure source 134 and the tissue site 114 to collect exudate and other fluids drawn from the tissue site 114. The canister 137 may couple a reduced-pressure source 134 to a reduced-pressure manifold 122 at a tissue site 114, and collect fluids from a wound at the tissue site 114. The canister 137 may be referred to as a reduced-pressure canister.

In the embodiment shown in FIGS. 1-3B, the canister body 142 includes a basin portion 144 and a lid portion 146. The lid portion 146 may be formed by a substantially planar exit wall 148 that is capable of mating with the basin portion 144. A basin wall 150 forms the basin portion 144 and includes curved contours to create a crescent shape. The basin portion 144 and lid portion 146 may instead form a canister body that is cylindrical, cubical, rectangular cubical, or any other shape. It should also be noted that the canister body 142 may not include separate basin and lip portions, but rather may be formed from a substantially unitary housing.

The canister body 142 includes an inlet 152 fluidly coupled to the reduced-pressure delivery conduit 112, and an outlet, or vent portion 160. The reduced-pressure treatment system 110 may include a canister filter or other in-line protection filter to prevent fluid from entering the reduced-pressure source 134. The vent portion 160 of the canister body 142 comprises a hydrophobic filter to prevent liquid from exiting the canister body 142 through the vent portion 160. The inlet 152 may be positioned on a wall 178 disposed in a recessed region 180 of the basin portion 144.

The hydrophobic filter of vent portion 160 prevents liquid egress from the canister body 142 while allowing gases or vapor to exit. A hydrophobic filter may be a hydrophobic membrane welded to the canister body 142 in a window or opening. Alternatively, a plurality of pores 162 are formed in the canister body 142 and covered with a hydrophobic coating (e.g., hydrophobic coating 271 of FIG. 7) to form a weld-free hydrophobic filter.

In such an embodiment, the vent portion 160 includes the integral hydrophobic filter formed within the exit wall 148. Integrating the vent portion 160, which includes or otherwise functions as a hydrophobic filter, into the exit wall 148 may be beneficial for a number of reasons. An integral hydrophobic filter removes the need to weld or fix a filter in place as a separate manufacturing step, thereby mitigating concerns related to welding a filter in place, using mechanical fasters, or using adhesives. Such concerns may include localized stresses, weaknesses associated with the weld(s), and material constraints associated with welded materials. In addition, an integral filter may reduce the overall cost of the reduced-pressure canister because fewer parts and less labor are needed to assemble a canister body 142 for use in a reduced-pressure treatment system 110 or other medical system requiring a reduced-pressure canister.

The vent portion 160 allows fluid communication between the canister body 142 and the reduced-pressure source 134 such that a collection chamber or reservoir portion 166 formed by the canister body 142 can maintain a reduced pressure. This reduced pressure may be transmitted to the tissue site (or other location for a medical application) through the inlet 152. In the reduced-pressure treatment system 110, the inlet 152 delivers the reduced pressure to the reduced-pressure delivery conduit 112, the tubing adapter 118, and the distribution manifold 122. The reduced pressure draws exudate and other fluids from the tissue site 114 into the canister body 142. The hydrophobic filter prevents liquids that that are drawn into the canister body 142 from exiting the canister body 142 through the vent portion 160 and contaminating the reduced-pressure source 134.

Figure 4:
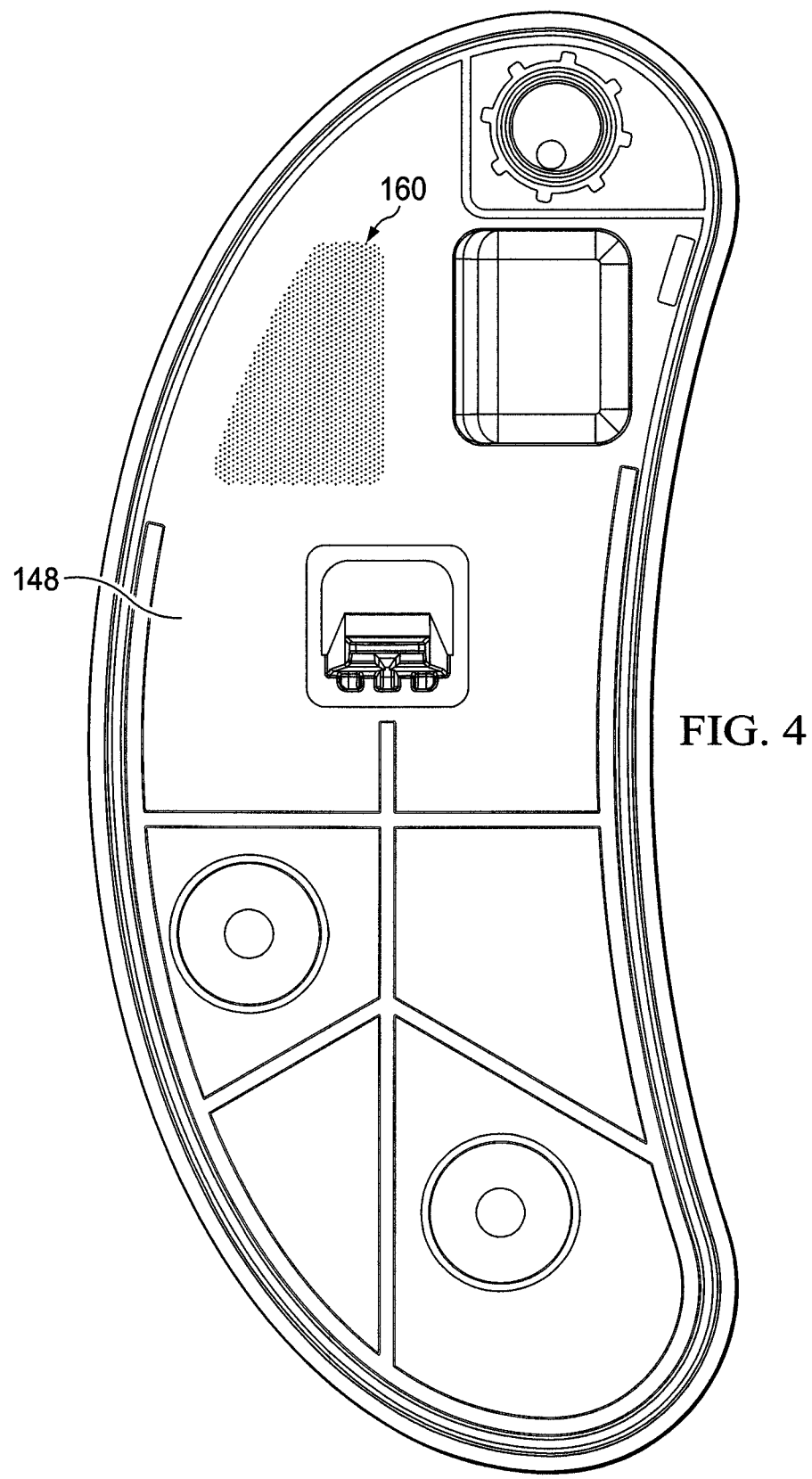
FIG. 4 is a schematic, side (interior) perspective view of a lid portion of the reduced-pressure canister of FIG. 1.
Figure 5A:
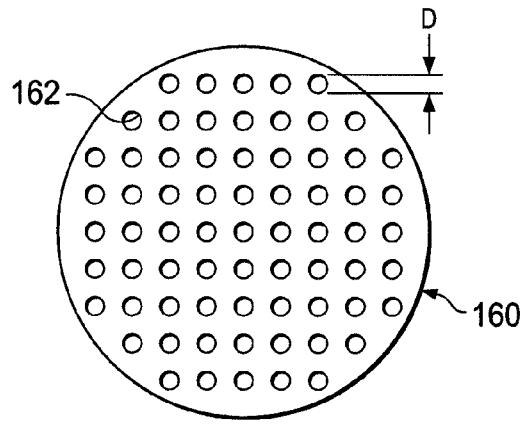
FIG. 5A is a schematic, detail view of a portion of a vent of a reduced-pressure canister.
Figure 5B:
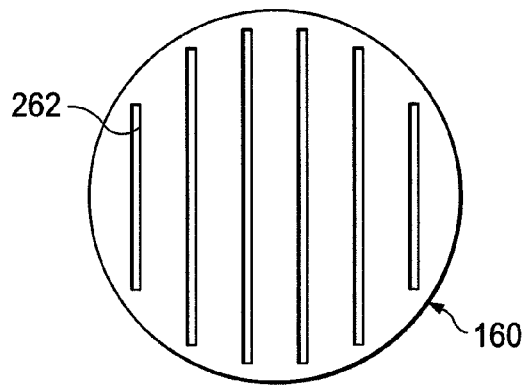
FIG. 5B is an alternative schematic, detail view of a portion of a vent of a reduced-pressure canister.
Figure 5C:
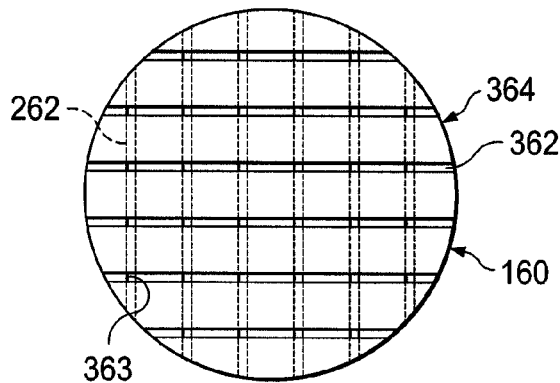
FIG. 5C is an alternative schematic, detail view of a portion of a vent of a reduced-pressure canister.
Figure 6B:
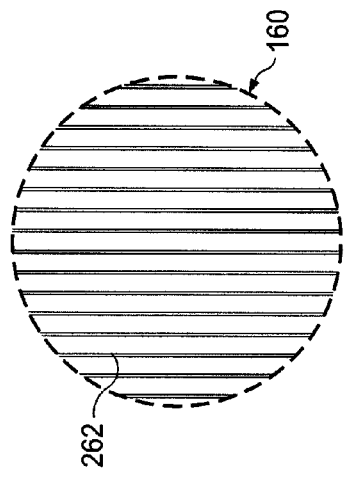
FIG. 6B is a schematic detail of FIG. 6A.

As discussed in more detail with regard to FIGS. 4-6, the vent portion 160 is formed with the plurality of pores 162, or apertures, formed within the exit wall 148, and a hydrophobic coating. The hydrophobic coating may be applied to the plurality of pores 162 to form the hydrophobic filter, which is integral to (i.e., formed within) the vent portion 160 and exit wall 148. No welds are required. The integral hydrophobic filter enables the vent portion 160 to function as a liquid-air separator and prevent liquids from passing through the exit wall 148 to the reduced-pressure source 134.

Referring now primarily to FIGS. 2, 3A, and 3B, the canister body 142 includes the collection chamber 166 or fluid reservoir for collecting fluid within the canister body 142. An entry chamber 170 is positioned above the collection chamber 166. An aperture 190 allows fluid communication between the entry chamber 170 and the collection chamber 166. The inlet 152 may be disposed in the wall 178 such that a primary lumen of the reduced-pressure delivery conduit 112 facilitates communication between the tissue site 114 and the entry chamber 170. The entry chamber 170 further includes a floor 186 that at least partially separates the entry chamber 170 from the collection chamber 166. Despite the presence of the floor 186, fluid communication is permitted between the entry chamber 170 and the collection chamber 166 through the aperture 190. The aperture 190 may be a slot, hole, channel, or any other aperture that allows communication between the entry chamber 170 and the collection chamber 166.

The positions and shapes of the inlet 152, vent portion 160, and entry chamber 170 may vary depending on the shape and configuration of the canister. As such, the positions and shapes of the inlet 152, vent portion 160, and entry chamber 170 may differ from the positioning, shapes, and general configurations described above and shown in the related FIGS. 1-7.

A baffle 156 may be provided to reduce the formation of protein bubbles, burst protein bubbles that have formed, and minimize the premature blocking of the vent portion 160. The baffle 156 may have a surfactant coating to reduce the surface energy of the bubbles.

FIG. 3B shows the path of fluid entering the canister body 142. Line 192 schematically depicts the fluid path. The fluid passes through the inlet 152 and into the entry chamber 170. Fluid leaving the entry chamber 170 is directed downward (for the orientation shown) through the aperture 190 at an end of the entry chamber 170. The fluid passes into collection chamber 166. As the fluid enters the collection chamber 166, gravity pulls any liquid in the fluid stream downward to collect in a bottom (for the orientation shown) portion of the collection chamber 166. Gases in the fluid stream may be pulled upward around the baffle 156 to exit the canister body 142 at the vent portion 160.

The baffle 156 creates a tortuous pathway (as illustrated, for example, by line 192) for fluid entering and traveling through the canister body 142. This tortuous pathway minimizes the risk of premature blocking of the hydrophobic filter by liquid entering the canister body 142. Additionally, the baffle 156 serves to prevent protein bubbles in the liquid exudate from forming or to block bubbles that have formed from reaching the vent portion 160. The baffle 156 also prevents or substantially reduces line-of-sight between the entry chamber 170 and the vent portion 160.

It should be noted that other means exist for creating a tortuous pathway for fluid entering the canister body 142. For example, a porous, reticulated foam such as a polyurethane foam may be positioned within the entry chamber 170. The reticulated nature of the foam minimizes bubble formation near the open end of the entry chamber 170, which limits protein deposition on the vent portion 160. Similarly, other foams or materials may be placed within the entry chamber 170 or between the entry chamber 170 and the vent portion 160 to prevent premature blocking of the hydrophobic filter. In canisters that may not include a separate entry chamber, a porous foam may be placed anywhere in the canister to prevent or reduce protein deposition on the vent portion 160.

Referring now primarily to FIG. 4, a schematic, side (interior) perspective view of the lid portion 146 of the canister body 142 of FIG. 1 is presented. FIG. 4 shows a vent portion 160 that may be formed on the inner surface of a lid portion 146 (or a wall) in a number of ways, as detailed in FIGS. 5A-5C. To form the vent portion 160, a plurality of pores 162 are formed in a portion of the exit wall 148 of the lid portion 146. The plurality of pores 162 may be micro-drilled, and as such may be generally circular in shape. In this illustrative embodiment, the exit wall 148 is a part of the lid portion 146 of the canister body 142 and may be formed in an injection molding process. The exit wall 148 is a flat area of accurate constant wall thickness where a filter can be located.

Referring now primarily to FIGS. 5A-5C, various alternative embodiments of vent portions 160 are presented. The vent portions 160 include or form an integral hydrophobic filter, i.e., a hydrophobic filter formed within the exit wall 148. In FIG. 5A, the vent portion 160 is formed from a plurality of pores 162 that are micro-holes formed in the exit wall 148. The pores 162 may be formed with an excimer laser or any other suitable manufacturing technique. The pores 162 may also be formed by photo or chemical etching. The diameter (D) of each of the plurality of pores 162 may be between 0.25 and 1 micron, or any other suitable size, and the quantity of pores 162 may be varied so that the cumulative flow rate through the pores 162 is sufficient for the flow of the system. The pores 162 may be formed in a pattern or randomly.

The pores 162 may be sized to function as a barrier to bacteria or viruses. In cases where the hydrophobic filter is intended to function as a barrier to bacteria, the plurality of pores 162 may have a diameter of, for example, 0.5 to 1 microns. In cases where the hydrophobic filter is intended to function as a barrier to a virus, the plurality of pores 162 may have a smaller diameter of, for example, 0.25 micron. The size of the pores may even be adjusted to provide protection against specific types of bacteria. Generally, holes of 1 micron in diameter, arranged in a tortuous path, are sufficiently small to prevent the passage of some bacteria and fluid through a hydrophobic filter operated at low level differential pressures.

FIG. 5B presents another illustrative embodiment in which the vent portion 160 is formed from a plurality of micro-slits 262 formed in the exit wall 148 instead of holes. The micro-slits 262 are sized with a lateral gap such that the micro-slits 262 function analogously to pores 162. The micro-slits 262 may be formed using any technique mentioned herein for the pores or machining.

FIG. 5C presents another illustrative embodiment that includes a separate grate member 364 that includes a second set of micro-slits 362, also shown in FIG. 6. The grate member 364 may be formed separately from the exit wall 148 and affixed to the exit wall 148 such that the micro-slits 362 of the grate member 364 substantially overlie and are perpendicular to the micro-slits 262 of the exit wall 148 grate. In such a configuration, the intersections of the micro-slits 262 and 362 will create a set of micro-holes 363 that allow gases to pass through the vent portion 160 of the exit wall 148. The micro-holes 363 function analogously to the pores 162. In another illustrative embodiment, the entire vent portion 160 may be formed in a grate member 364 that may be sealably coupled to an open area in an end wall 148 of a canister body 142.

Desired hydrophobic properties may be given to the vent portion 160 by applying a surface treatment process to the vent portion 160 of the reduced-pressure canister over the apertures, e.g., pores 162, micro-slits 262, or micro-holes 363. An example of such a surface treatment process is shown in FIG. 7 below.

Figure 6C:
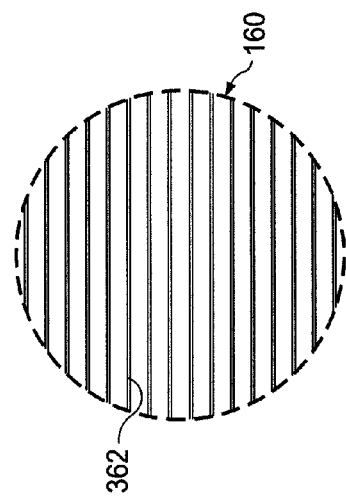
FIG. 6C is a schematic detail of FIG. 6A.
Figure 6A:
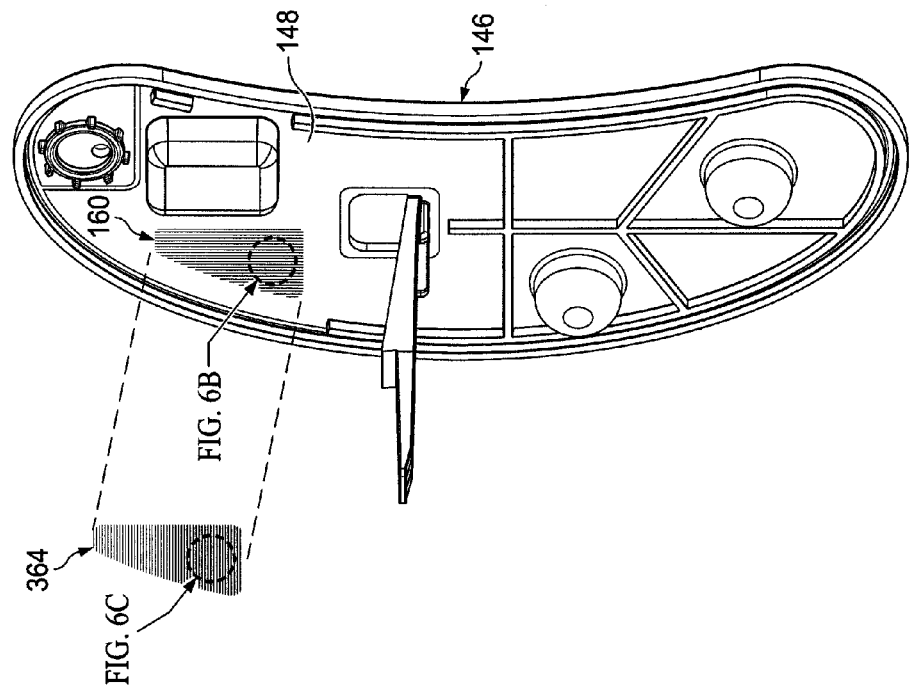
FIG. 6A is a schematic, partially-exploded, perspective view (interior facing) of a lid portion of a reduced-pressure canister having a grate member.

Referring now to FIG. 6A, an illustrative lid portion 146 of a canister 137 is presented with a plurality of micro-slits 262 formed in the exit wall 148 on a vent portion 160. A grate member 364, which has a plurality of micro-slits 362 as shown in FIG. 6C, is coupled to exit wall 148 over the micro-slits 262 to form a plurality of micro-holes analogous to micro-holes 363 of FIG. 5C. Similar to other illustrative embodiments herein, the plurality of holes may be covered with a hydrophobic coating.

Figure 7:
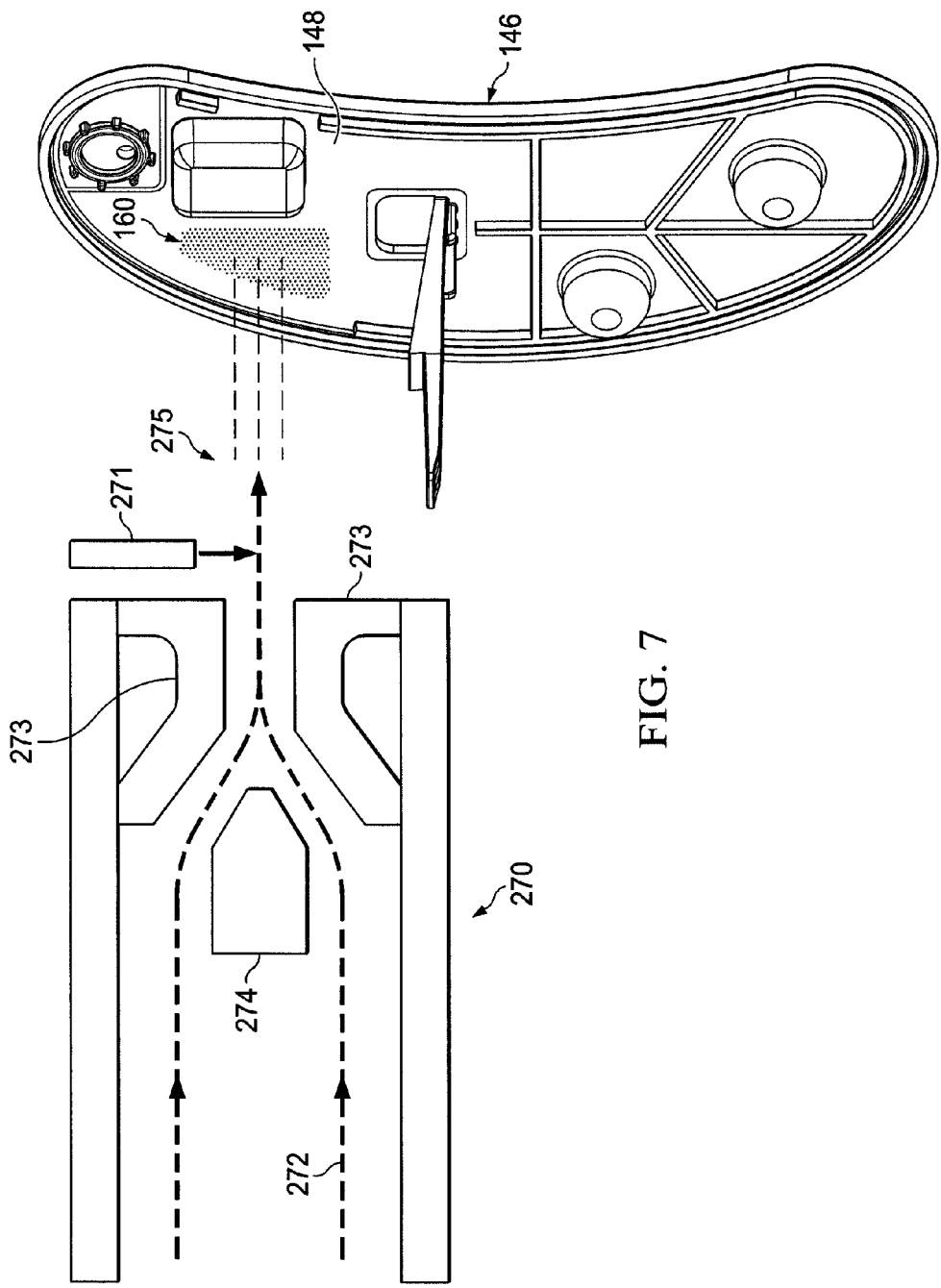
FIG. 7 is a schematic diagram, with a portion shown as a perspective view, of a plasma treatment process for applying a hydrophobic coating to a vent portion of a reduced-pressure canister.

Referring now primarily to FIG. 7, one illustrative process for delivering a hydrophobic coating is presented. In particular, a lid portion 146 of a reduced-pressure canister is presented being treated in a plasma treatment chamber (not explicitly shown). In the plasma treatment process, a plasma coating unit 270 receives a gas 272 and passes the gas 272 between a nozzle that includes a cathode 274 and anode 273.

An arc between the cathode 274 and anode 273 ionizes the gas and causes the gas to dissociate and form a plasma stream 275, into which the coating material 271 is injected. The plasma stream heats the coating material to a workable or depositable state. Other processes for delivering the hydrophobic coating may be used. For example, in another plasma process for applying the hydrophobic coating, the item to be coated may be placed within a chamber into which the treatment chemical is introduced and ionized.

The heated plasma stream 275 cools as the plasma stream 275 moves away from the plasma coating unit 270. The work piece, e.g., the canister lid portion 146, is some distance away from the plasma coating unit 270 where the canister lid portion 146 can receive the coating material 271 at an ideal temperature for deposition. According to an illustrative embodiment, a plasma deposition process deposits a hydrophobic coating onto the vent portion 160 portion of the lid portion 146 of the canister 137. The coating may be a fluorocarbon, heptadecafluorodecylacylate, acrylates containing haloalkyl (e.g., fluoroalkyl) or perhaloalkyl (e.g. perfluoroalkyl) groups, hexamethyldisiloxanes, and other substituted hydrocarbons, such as 1,2-epoxy-3-phenoxy-propane. In the plasma treatment process, the hydrophobic coating chemically bonds to the substrate, i.e., to the exit wall 148 of the lid portion 146 of the canister, to resist mobility or removal of the hydrophobic coating from the substrate.

In most applications, it is undesirable that any liquid pass through the vent portion 160 to the reduced-pressure source 134. As such, the reduced-pressure treatment unit 136 may include a pressure sensor that monitors the pressure of the reduced-pressure treatment unit 136. Where a canister includes a hydrophobic filter, the hydrophobic filter prevents liquid from passing through the exit wall until the pressure differential between the fluid reservoir of the canister body 142 and the reduced-pressure treatment unit 136 reaches the breakthrough pressure of the filter, "P(b)." As such, the reduced-pressure unit may monitor the pressure differential between the canister body 142 and the reduced-pressure treatment unit 136. Before the pressure differential reaches the breakthrough pressure, P(b), of the hydrophobic filter, the reduced-pressure treatment unit 136 may deactivate the reduced-pressure source, thereby preventing fluid from entering the reduced-pressure treatment unit 136.

The breakthrough pressure, P(b), of a hydrophobic filter resulting from the plasma treatment process is a function of the size of the holes that form the filter, the surface tension of the liquid, and the contact angle of the surface. In turn, the contact angle of the surface is a measure of the hydrophobicity of the surface. Here, the equation "P(b)=4 g(cos q)/D" defines the breakthrough pressure of the hydrophobic filter, where g is the surface tension of the liquid, q is the contact angle between the liquid and the surface, and D is the diameter of a pore. In one illustrative, non-limiting example, the hydrophobic filter has a "water breakthrough pressure" of approximately 500 mm Hg. As a result of forming the hydrophobic filter in a plasma treatment process, the deposited hydrophobic coating may advantageously show higher water repellence than more traditional PTFE based filters that provide an effective oleo-phobic or hydrophobic coating.

Neutralizing odors may also be a concern when collecting fluids from a wound in a reduced-pressure treatment system. To neutralize odors associated with the wound fluid, a charcoal filter may be welded in place above the plurality of pores 162 on the internal face of the lid portion 146 of the canister body 142. Use of the charcoal filter helps to ensure that air moved through the holes does not cause odor. A charcoal filter may also be welded into the same location on the external sealing face of the canister body 142. In one embodiment, a charcoal coating may be applied to or included in a portion of the canister body 142, which may include the vent portion, using a plasma surface treatment similar to the process described with regard to FIG. 7.

As described herein, the canister body 142 primarily collects exudate from the tissue site 114 or functions to collect liquid in other medical applications. Exudates from a small percentage of patients have unique chemical and physical properties. These properties promote bubble formation and foaming as fluid enters the canister, and the fluid may contain proteins that can adhere to many hydrophobic filter membranes. Under normal conditions, the protein film builds up gradually but protein film build-up may be exacerbated by the presence of foaming that causes the exudate to bubble. The presence of "exudate bubbles" maximizes the rate of protein adherence by atomizing minute droplets of protein-containing exudate when the bubbles pop. The small size of these droplets limits the liquid-shedding effects of the hydrophobic filter, and encourages their rapid evaporation. Evaporation of the droplets results in a protein residue being left behind on the surface where the droplets were located. When the residue accumulates on the surface of a hydrophobic filter, the residue impairs filter performance and airflow. This blockage can occur after collecting only a fraction of the canister's capacity, necessitating premature disposal of the canister and increasing operating costs. Under severe conditions, the filter can become completely occluded, which causes the system to fail to deliver the intended treatment. In the extreme case, the occlusion can lead to complete failure of the filter membrane, defeating the primary requirement of separating the fluid from the air, and permitting contamination of downstream components.

As an additional means to prevent occlusion of the vent portion 160 and associated hydrophobic filter, the vent portion 160 may be coated with a protease during the plasma treatment process. The protease coating has the effects of an enzyme and may cause protein breakdown in the area of the filter to prevent build up and blockage of the filter. Such a coating may act as an anti-fouling layer in addition to preventing proteins from clogging the filter.

In addition to forming an integral hydrophobic filter as an aspect of the vent portion 160, during the plasma treatment process other coatings may be applied to other portions of the canister body 142 by applying alternate coatings. For example, other portions of the canister body 142 may be coated with solidifying agents to stabilize or change the state of liquids that are collected in the canister body 142. Such a coating may reduce the need for a super-absorbent pouch in some reduced-pressure treatment systems. Similarly, the inside of a canister body 142 may be coated with a bactericide that would kill or render bacteria inactive and reduce or eliminate odors. A charcoal coating may also be applied to reduce the need for the charcoal filter to eliminate odors.

In addition, the reduced-pressure conduit may be treated using a plasma treatment process so that fluids entering the conduit and canister body experience less drag when entering the canister. This type of coating may increase the efficiency of the tube and in turn increase the ability of the reduced-pressure treatment unit to function more accurately and efficiently.

A hydrophobic filter that is integral to the canister body 142 may have other beneficial attributes as compared to a welded filter or a filter assembled to the canister body using another manufacturing process. For example, a wider selection of materials may be available to form the filter because the material will not need to be welded. Further, the filter can be formed on surfaces that are less conducive to welding, allowing a filter to be easily formed within a curved canister wall. In the case of a welded filter, the weld may also present a point of weakness in the canister and a bad filter weld can result in the ingress of liquids to the reduced-pressure treatment unit.

A plasma treatment process coating may also be "gamma stable," i.e., able to withstand gamma radiation without being destabilized. Some materials used to create hydrophobic coatings, such as PTFE, may not be able to sustain gamma radiation without undergoing undesirable changes in their polymer structure. In the plasma treatment process, materials other than PTFE may be more easily applied. For example, heptadecafluorodecylacylate, a more gamma stable polymer, may be applied using the plasma treatment process. As such, a hydrophobic filter element can be made that withstands sterilization using gamma radiation without breaking down. In addition, the plasma coated solution has the beneficial attribute of being immobile once deposited. The applied coating will bond and coat the entire surface of the vent portion 160, including the internal surfaces of micro holes or other apertures that have been formed in the lid portion 146 (e.g., pores 162). The coated pores 162 may provide an even greater repellence to liquid entry because the pores 162 will have a nominally smaller diameter, thereby increasing the breakthrough pressure, P(b), of the filter. The surface tension of any liquids that come into contact with the pores 162 will also have to be overcome in order for fluid to pass through the filter.

The plasma treatment process can be used to apply multiple coatings to apply different chemical groups, offering a plurality of functionality. As such, hydrophobic, hydrophilic, anti-protein, and anti-bacterial coatings may be applied.

According to an illustrative embodiment, a method for forming a hydrophobic filter within a reduced-pressure canister body is further provided. The method includes forming a canister body 142 with a designated area to serve as a vent portion 160. The method also includes perforating the designated area to populate the area with very small apertures, for example pores 162 having a diameter of between 0.25 and 1 microns. To give the area the properties of a hydrophobic filter, the method involves applying a hydrophobic coating to the designated area as previously described. In an embodiment, the hydrophobic coating is a fluorocarbon, such as heptadecafluorodecylacylate.

The integral hydrophobic filter of the canister body functions as both a fluid outlet and a liquid-air separator that allows gases to flow out of the canister but retains liquids within the canister. The method may include minimizing the susceptibility of the filter to occlusion resulting from the deposition of proteins from the wound exudate on the vent portion 160. Minimization or prevention of protein deposition may occur in several different ways, including by providing a baffle or porous foam, or by depositing a protease with the hydrophobic coating of the canister. In this way, protein deposition may further be minimized or prevented by preventing proteins from reaching the hydrophobic filter or by enzymatically breaking down any proteins that reach the filter.

It will be appreciated that the illustrative embodiments described herein may be used with reduced-pressure treatment systems of any type, shape, or size and similarly with canisters of any type, shape, or size. The location of the inlet, outlet, and vent portion with an integral hydrophobic filter may also vary depending upon the particular reduced-pressure canister design. Similarly, the geometry of the vent portion and hydrophobic filter may be modified as necessary to conform to the contours or configuration of the reduced-pressure canister. It should also be noted that the vent, portion and hydrophobic filter are not limited to use with a reduced-pressure treatment system. The vent portion and hydrophobic filter may also be used with other medical collection canisters that include liquid-air separators.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A reduced-pressure treatment system comprising:
a reduced-pressure canister comprising:
   a basin,
   a lid configured to mate with the basin to form a fluid reservoir, the lid having a plurality of apertures formed within, and integral with, an exit wall of the lid, each aperture extending through the exit wall of the lid and being in fluid communication with the fluid reservoir,
   an inlet for receiving fluids from a patient, the inlet in fluid communication with the fluid reservoir, and
   a hydrophobic coating applied to the plurality of apertures;
a reduced-pressure source fluidly coupled to the fluid reservoir through the plurality of apertures; and
a reduced-pressure delivery conduit fluidly coupled to the inlet for delivering fluids from the patient to the reduced-pressure canister.

2. The system of claim 1, wherein the plurality of apertures comprise a plurality of pores having a diameter in between about 0.5 and about 1 micron.

3. The system of claim 1, wherein the hydrophobic coating comprises a fluorocarbon.

4. The system of claim 1, wherein the hydrophobic coating comprises a coating selected from a group consisting of heptadecafluorodecylacylate, acrylates containing haloalkyl groups, acrylates containing perhaloalkyl groups, hexamethyldisiloxanes, and 1,2-epoxy-3-phenoxy-propane.

5. The system of claim 1, further comprising an anti-microbial coating over the plurality of apertures.

6. The system of claim 1, further comprising an anti-bacterial coating over the plurality of apertures.

7. The system of claim 1, further comprising a protease coating over the plurality of apertures.

8. The system of claim 1, further comprising a charcoal coating over the plurality of apertures.

9. The system of claim 2, wherein the plurality of apertures have a breakthrough pressure of about 500 mm Hg.

10. A reduced-pressure canister comprising:
   a basin;
   a lid comprising a plurality of apertures, the lid configured to mate with the basin to form a fluid reservoir in fluid communication with each of the plurality of apertures formed within, and integral with, an exit wall of the lid, each aperture extending through the exit wall of the lid;
   an inlet fluidly coupled to the fluid reservoir for receiving fluids from a patient; and
   a hydrophobic coating applied to the plurality of apertures.

11. The reduced-pressure canister of claim 10, wherein the plurality of apertures comprise a plurality of pores, each pore having a diameter of about 0.5 to about 1 micron.

12. The reduced-pressure canister of claim 10, wherein the plurality of apertures comprise a plurality of parallel slits.

13. The reduced-pressure canister of claim 12, wherein the plurality of parallel slits comprise a first plurality of parallel slits, the reduced-pressure canister further comprising:
   a grate member having a second plurality of parallel slits, the grate member having a hydrophobic coating; and
   wherein the grate member couples to the lid over the first plurality of parallel slits so that the second plurality of parallel slits substantially overlies and is perpendicular to the first plurality of parallel slits.

14. The system of claim 1, wherein the plurality of apertures comprise a plurality of parallel slits.

15. The system of claim 14, wherein the plurality of apertures further comprise:
   the plurality of parallel slits being a first plurality of parallel slits;
   a grate member having a second plurality of parallel slits, the grate member having a hydrophobic coating; and
   wherein the grate member couples to the lid over the first plurality of parallel slits so that the second plurality of parallel slits substantially overlies and is perpendicular to the first plurality of parallel slits.

16. The system of claim 1, wherein the plurality of apertures comprise a plurality of micro-holes.

17. The system of claim 1, wherein each micro-hole of the plurality of micro-holes has a diameter between about 0.25 and about 1 micron.

18. The canister of claim 10, wherein the plurality of apertures comprise a plurality of micro-holes.

19. The canister of claim 10, wherein each micro-hole of the plurality of micro-holes has a diameter between about 0.25 and about 1 micron.

\* \* \* \* \*